United States Patent [19]
Elson

[11] Patent Number: 5,409,667
[45] Date of Patent: Apr. 25, 1995

[54] TUBE RACK

[76] Inventor: Edward E. Elson, 4356 Claytor Cir., Anaheim, Calif. 92807

[21] Appl. No.: 236,658

[22] Filed: Apr. 29, 1994

Related U.S. Application Data

[63] Continuation of Ser. No. 61,572, May 13, 1993, abandoned.

[51] Int. Cl.$^6$ .............................................. B01L 9/06
[52] U.S. Cl. ............................ 422/104; 211/60.1;
211/71; 211/74; 211/79; 422/102
[58] Field of Search ............. 422/99, 102, 104;
211/601, 71, 74, 79

[56] References Cited

U.S. PATENT DOCUMENTS

| | | | |
|---|---|---|---|
| 1,859,879 | 3/1932 | Harlan | 211/71 |
| 2,979,210 | 4/1961 | Patterson | 211/74 |
| 3,375,934 | 4/1968 | Bates | 211/74 |
| 3,390,783 | 7/1968 | Quackenbush | 211/74 |
| 3,649,462 | 3/1972 | Jessup | 422/104 |
| 3,802,844 | 4/1974 | Sendra et al. | 422/104 |
| 4,055,396 | 10/1977 | Meyer et al. | 422/104 |
| 4,407,958 | 10/1983 | De Graff, Jr. | 422/104 |
| 4,453,639 | 6/1984 | Sharma | 422/104 |
| 5,128,105 | 7/1992 | Berthold et al. | 422/104 |
| 5,141,117 | 8/1992 | Olsen et al. | 211/71 |

OTHER PUBLICATIONS

Bio-Rad Catalog, p. E7, Bio-Rad Labs Chemical Division, Feb. 1990.

*Primary Examiner*—Timothy M. McMahon

[57] ABSTRACT

A portable rack for medical or laboratory tubes where it is desirable that the tubes be supported in either generally vertical or generally horizontal positions as the user desires. The illustrated rack includes a center panel having openings for receiving the tubes and a pair of end panels, one longer and one shorter. The geometry of the holder allows the holder to be supported with the larger end panel resting on a supporting surface so as to position the tubes extending generally horizontally. The geometry of the rack further allows the rack to be positioned upon the unattached edges of the side panels so that the tubes are held generally upright. A handle is provided for carrying the rack so that the tubes will be extending generally horizontally. The openings are shaped to hold the tubes in a fixed rotational orientation as may be desired for particular tubes.

32 Claims, 2 Drawing Sheets

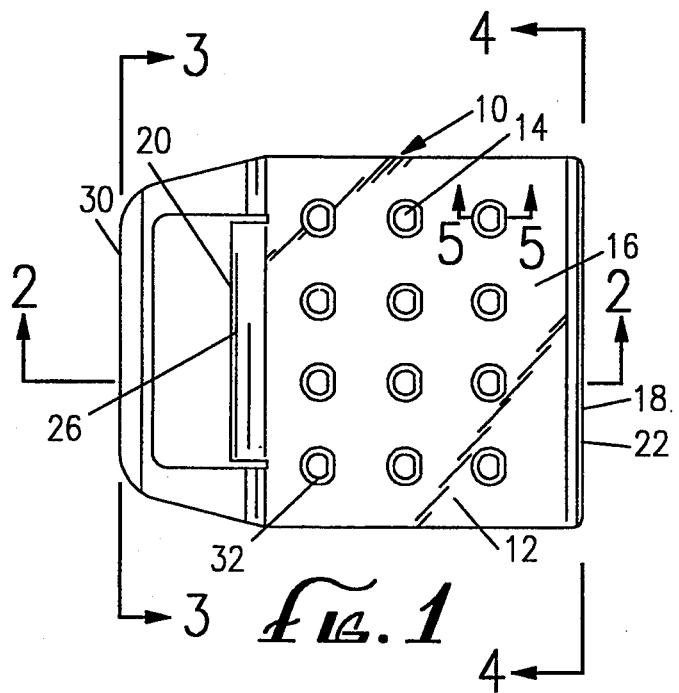
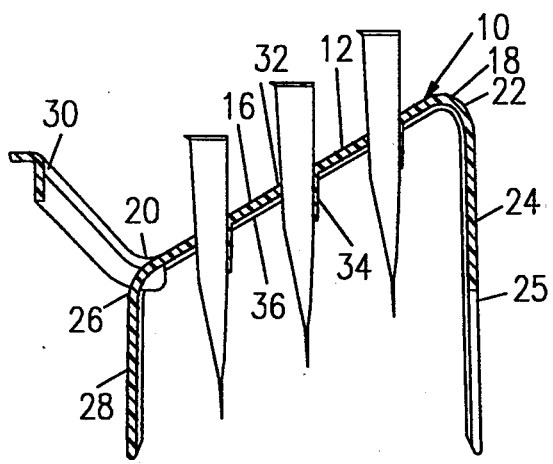 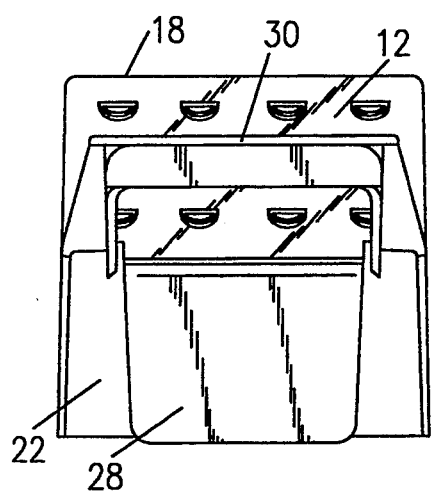

TUBE RACK

This is a continuation, of application Ser. No. 08/061,572, filed May 13, 1993 now abandoned.

FIELD OF INVENTION

Portable racks or holders for medical or laboratory tubes such as those containing urine samples.

BACKGROUND OF INVENTION

At times may be important to hold and/or transport medical or laboratory tubes in either a generally upright vertical orientation or in a generally horizontal orientation, and to be able to quickly and easily change between the two orientations. One such tube with such requirements is a urine sample tube recently developed and sold by the assignee of this application under the trademark CEN-SLIDE ®. This particular tube is disclosed in detail in U.S. Pat. Nos. 5,030,421 and 4,865,812.

Briefly, this tube has an elongated generally tubular tapered body. The larger end is open and is provided with a suitable closure. The smaller end is connected to a generally flat rectangular viewing slide panel or section. The viewing section has a thin flat interior compartment that is in communication with the smaller end of the tubular body.

The tube is adapted to be mounted in a centrifuge with the tube extending outwardly and downwardly from the axis of rotation at about a forty-five degree angle. The tube is oriented so that the flat slide viewing section lies in a vertical or upright plane. As the tube is rotated by the centrifuge, the viewing section is lightly engaged by suitable means in the centrifuge to apply a tapping or flicking action to the viewing section. This action helps to evenly distribute cells and/or sediment from the urine sample evenly throughout the interior compartment of the viewing section.

It is highly desirable that, after the centrifuging, the tube then be maintained with the plane of the viewing section generally horizontal while the tube is being transported to the microscope and when the rack holding the tube is set down by the microscope. This allows the cells and other matter dispersed over the viewing section to settle into horizontal layers extending across the viewing section. The viewing section then serves as a viewing slide that can be positioned under the microscope to observe the sample within the viewing section compartment.

In addition, prior to centrifugation, it is desirable that the tube be maintained in a generally upright or vertical orientation so that it can be conveniently filled and so that added material such as reagents, stains, dip strips and the like may be inserted into the open larger end of the tube.

It is also important that the surfaces of the slide section not be impacted and thus scratched while the tube is being supported or transported.

Further, it is highly desirable that the tubes as well as their contents be fully observable from all angles while they are being supported. For example, this allows ready identification of particular tubes and also continued observation of the condition of the various tubes at various times.

Prior art racks or holders tended to hold sample tubes in either an upright or a horizontal position, and not selectively in either of those positions. Such prior art racks normally had openings larger than the cross section of the tube and relied on a support plate or other support structure to engage and support the lower inserted end of the tube. This could result in scratching or marring the sensitive viewing surfaces of the viewing panel of the CEN-SLIDE ® sample tube or comparable tubes.

Such prior art racks were normally opaque and thus provided limited visibility of the tubes and the contents of the tubes.

The prior art racks normally included holding or handle means that supported the rack so that the tubes were held in a generally upright or vertical position. As noted above, supporting the centrifuged CEN-SLIDE ® sample tubes in such a vertical position, with the slide viewing panels in a generally upright plane, while the tubes were carried from one location to another could undesirably change or distort the sample within the viewing panel. In this connection, the array of cells and other particulate components disbursed in the specimen sample in the slide panel would tend to shift and congregate toward the lower end of the viewing panel.

SUMMARY OF THE DISCLOSURE

The present invention contemplates a novel and improved rack or holder for selectively holding elongated tubes with their axes either in a generally horizontal or a generally vertical orientation. Further, the similarity in size and shape of the tubes and the matching holes in the rack prevents the tubes from falling out of the rack when the tubes are carried in a generally horizontal position.

The illustrated rack is designed to hold an elongated but somewhat tapered tube, the tube having a larger openable end and a smaller closed end, in an upright position in the rack without the use of any underlying supporting plate or structure that would engage and might damage the lower end portion of the tube. The illustrated rack may be placed on a horizontal supporting surface in alternate selectable positions that will support the tubes with their axis either generally upright or generally horizontal as the user desires.

The illustrated rack includes a central panel with a plurality of the openings, a long leg or side panel, and a short leg or side panel. These elements could also be considered "end panels." For ease of description, however, they will be called "side panels" throughout the specification. The side panels are connected to opposite edges of the tube holding central panel. When the rack is supported on a generally horizontal surface upon the long end or side panel, the tubes are generally horizontal. When the rack is supported on the outer unattached edges of the two end or side panels, the tubes are generally upright or vertical. When the handle is grasped and the rack is carried by the handle, the weight of the rack and the tubes will orient the rack and the tubes so that the axes of the tubes are generally horizontal or slightly inclined from the horizontal with the larger ends of the tubes slightly elevated above the smaller ends.

The illustrated rack is constructed to minimize the risk that the tubes will fall out of the rack while it is being carried. First of all, the tubes are oriented with their axes between true horizontal and slightly inclined so that the tube smaller end is slightly lower than the larger end. The phrase "generally horizontal" is used herein to refer to such orientation. The illustrated CEN-SLIDE ® sample tubes are tapered from the larger open end toward the smaller closed end and thus, produce a wedge-like fit with the mating opening in the rack, which tends to maintain the tube seated in the opening of the rack. The illustrated tube is made of a slightly flexible resilient material which enhances the wedge-like engagement between the tube and rack opening. Further, each opening in the illustrated rack does not extend at a right angle to the rack panel, but is somewhat inclined from that right angle so that the tube assumes the generally horizontal position when the rack is being carried. Each opening can also be provided with a partial elongated portion that extends in the direction of the smaller closed end of the tube. The extension serves to support the tube when it is in a generally horizontal position. Further, while the partial elongated portion is preferably made of the same material of the carrier, it can be of a slightly flexible, resilient material or coated with such a material which tends to actively grip the adjacent portions of the tube.

The openings in the illustrated rack are formed to limit rotation of the tubes in the openings. As noted above, the CEN-SLIDE® sample tubes each have a flat viewing panel and a tubular body portion. The body portion has a flat side that is normally on the bottom that gives the body portion a D-shaped cross section. Such flat side is aligned with one face of the viewing panel. The illustrated openings have mating D-shaped outlines. The flat sides of the D-shaped openings are parallel to the outer face of the long side so that when the rack is resting upon that long side, the viewing panels extend generally horizontally.

The illustrated rack is made of a clear transparent material that allows full and clear visibility of the tubes themselves and of the contents of the tubes from all angles.

IN THE DRAWINGS

FIG. 1 is a top plan view of a tube support rack that embodies features of the invention.

FIG. 2 is a transverse side sectional view of the tube support rack taken generally along line 2—2 of FIG. 1, the rack holding several centrifuge tubes.

FIG. 3 is an end view taken generally along line 3—3 of FIG. 1.

DETAILED DESCRIPTION OF THE DRAWINGS

Figures 4, 5:
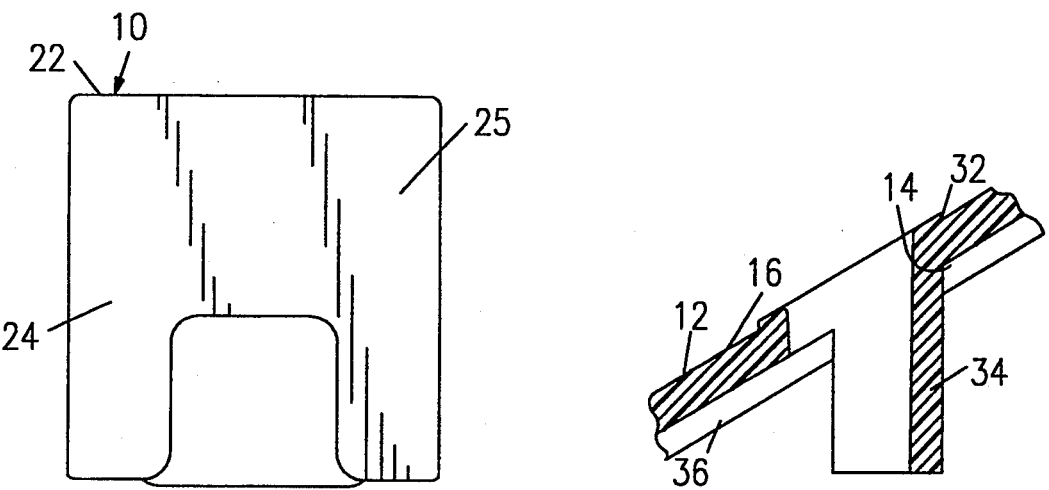
FIG. 4 is an end view taken generally along line 4—4 of FIG. 1.
FIG. 5 is an enlarged detailed view of the portion of FIG. 1 designated 5—5 of that drawing.

The drawings illustrate a tube holding and transporting rack 10 which embodies features of the invention. The illustrated rack 10 comprises a central tube holding section or panel 12 that has a plurality of openings 14 each sized and shaped to receive one of the tubes. The central panel 12 has an upper or outer surface 16 into which the tubes are inserted (and withdrawn). The central panel 12 is generally rectangular, having a pair of opposed longitudinal edges 18, 20. Along one of these longitudinal edges 18, the central panel is connected to a longitudinal edge 22 of a relatively long side or leg panel 24. The long side panel 24 has an outer face or surface 25 which may rest upon a horizontal support surface to support the rack with the tubes generally horizontal. Along the other or opposite longitudinal edge 20, the central panel 12 is connected to a longitudinal edge 26 of a relatively short panel 28. As best seen in FIGS. 3 and 4, the short panel 28 is generally rectangular, while the long panel 24 is generally U-shaped, having a pair of legs that extend outwardly away from the edge 22, edge 22 being connected to edge 18 of the central panel 12.

Figure 6:
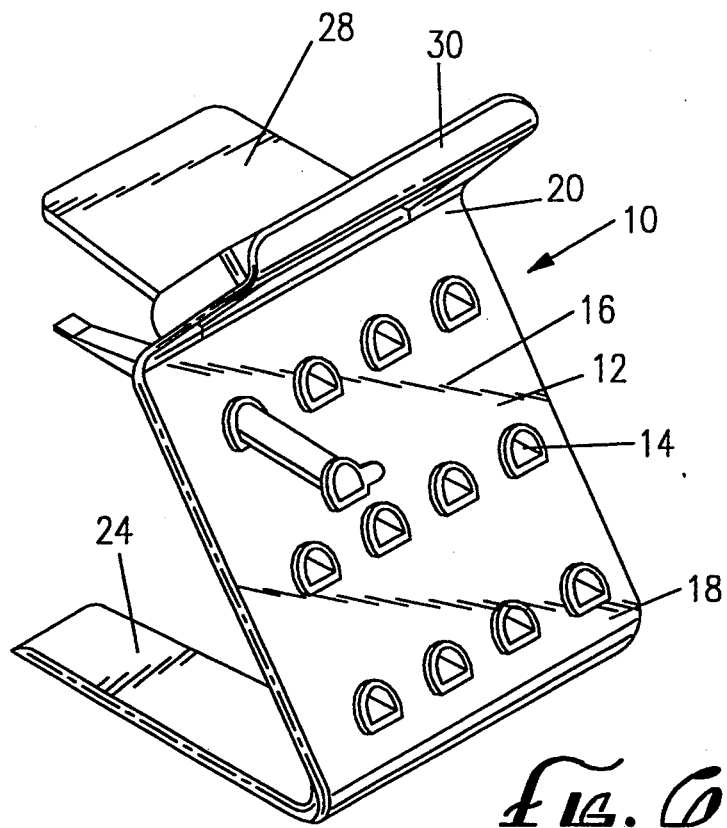
FIG. 6 is a perspective elevated side view of the rack in its horizontal position holding two CEN-SLIDE® tubes.

The illustrated rack 10 also includes a handle portion 30 which is generally U-shaped (FIG. 1) and connects to the other panels at approximately the intersection between the central panel 12 and the short panel 28. The geometry of the rack 10, in particular the angles between central tube holding sections 12, the long side panel 24 and the handle portion 30, is such that when the rack is carried by its handle 30, or the rank is rested on the outer surface 25 of the long side panel 24, the tubes mounted on the central portion 12 extend generally horizontally or slightly inclined with their larger ends slightly elevated (FIG. 6).

The rack 10 may be conveniently formed from a single piece of molded or otherwise formed plastic material which may be either thermoplastic or thermoset. A particular preferred material for the illustrated rack is a clear transparent acrylic multipolymer plastic material known by the trademark "Cyrolite G20." However, other structural plastics can be used to form the rack.

The illustrated rack 10 is specially designed for use with urine specimen tubes known by the trademark CEN-SLIDE®. As noted above, these tubes have a body that is generally tubular and tapered from a larger open to a smaller end. The larger end may have a suitable closure. The smaller end is formed into a generally flat rectangular slide viewing panel or portion. The slide panel has a very thin interior compartment that is in communication with the interior of the tubular portion. The tube body has a flat outer surface or face that is generally aligned with a flat outer face or surface of the slide panel. This gives the body or tubular portion of the "Censlide" tube a D-shaped cross section.

The openings 14 in the center tube holding panel 12 have a mating D-shaped cross section as shown best in FIG. 1. Each of the openings 14 has an enlarged rim 32 at the outwardly facing surface 16.

When a CEN-SLIDE® sample tube is inserted into an opening 14, the taper of the tube limits the distance that the tube can be inserted and serves to seat or support the tube in the opening. This can be readily seen in FIG. 2 where the tubes are supported in generally upright or vertical orientation. When the rack 10 is carried by the handle 30, and the tubes assume a generally horizontal orientation, the taper of the tubes and the mating openings 14 tend to provide a wedge-like engagement that provides a slight holding force on the tubes to maintain them in their position in the opening. As noted above, the illustrated rack 10 can be made of a somewhat flexible, resilient material, or coated with a less stiff material, such as used to form the CEN-SLIDE® sample tubes. This flexible resiliency of the tubes and the rack can aid in the holding of the tubes in the openings.

Each of the openings 14 is provided with a generally elongated or cylindrical partial section 34 that extends from a lower face 36 of the center panel 12, the lower face 36 being at a surface that is opposite from the center panel outer face 16. The elongated section or extension 34 can be seen best in FIGS. 2 and 5. This extension 34 serves to provide support to a tube in the associated opening 14 when the tube is held in a generally horizontal position. In addition, as shown in FIG. 2, the curvature of the extension 34 can extend beyond the center axis of the opening 14 so that it somewhat encircles and thus grasps the tube. Due to its curvature, geometry and/or resilient flexibility, and the resilient flexibility of the tube, the extension tends to lightly grasp and hold the tube inserted in the associated opening 14 to further maintain the position of the horizontal tube within the opening. It is desirable that the grip or wedging affect between the rack 10 and the tube be such that the tube can be easily and readily withdrawn from a seat position in the rack with mild pulling pressure from a thumb and one or two fingers. This can be further improved by forming the opening 14 and the elongated section 34 with a taper to match the taper of the tube.

As noted above, it is important that the slide panel of the CEN-SLIDE® sample tube be maintained generally horizontal while it is being transported from the centrifuge to the microscope and when the rack is set down at the location of the microscope. To accomplish this, such opening 14 has a generally D-shaped configuration which mates to the cross section of a CEN-SLIDE® sample tube, thus preventing rotation of the tube. This orients and holds the tube with the plane of the tube viewing panel generally parallel to the planes of the side panels 24, 28 and in a generally horizontal orientation (or slightly below horizontal) while the rack is being carried or while it is resting on the outer face of the longer side panel 24.

It has been found that very satisfactory results are obtained with the following rack geometry: The angle between the central panel 12 and the long side panel 24 is slightly less than 60° or approximately 59° and the angle between the central panel and the short side panel 28 is slightly greater than 120° or approximately 121°. The long and short side panels are generally parallel to one another. The angle between the central panel 12 and the handle 30 is about 102°, resulting in an angle between the handle 30 and the long panel 24 of slightly less than about 45° or about 43°. Further, the axes of the openings 14 and the extensions 34 are approximately parallel to the planes of the side panels 24, 28.

In operation, the rack 10 can be positioned resting on the free edges of the side panels 24, 28, generally as shown in FIG. 2. Then the tubes can be inserted vertically into the openings 14. The specimens in the tubes can be worked on as by adding reactants, dyes, or test strips as desired. The tubes are then closed and the rack can be carried by the handle 30 to the centrifuge. The tubes are then removed from the rack and go through the centrifuge process. The tubes are then returned to the rack in horizontal orientation. The rack and tubes can then be carried from the centrifuge to the location of the microscope, with the tubes remaining in a generally horizontal orientation as shown in FIG. 6. As noted above, the tubes can be horizontal or slightly tilted with the larger end slightly elevated. This maintains the slide panels generally horizontal and maintains the integrity of the specimen within the slide panel. During microscopic examination, the rack can be rested on the long side panel 24 and the tubes removed from the rack and examined as desired.

Various modifications and changes may be made in specific details of the illustrated rack without departing from the spirit and scope of the present invention. For example, the rack may be fabricated from multi sections which are independently molded or shaped or machined or otherwise made and then glued or heat-formed to one another. Further, the geometry, proportioning and the like of the rack may be revised in various ways so that the objective of selectively supporting tubes in either a generally horizontal or a generally vertical position is maintained, the horizontal position being provided particularly while the rack is carried from the centrifuging operation. The illustrated construction for defining and maintaining the orientation of the tubes is simple economical and highly desirable. However, other alternative means may be provided for particular applications, as for example manually operable locking mechanism can be used to positively lock the tubes in the rack. Similarly, the particular shape of the handle and of the various panels can be modified for various applications. Further, while the openings 14 have been shown as specifically shaped and sized to receive the CEN-SLIDE® tube, it is contemplated that the tube rack can be used for any shape tube, the shape of the hole, the orientation of the hole, and the extension 34 and the angle between the handle 30, central panel 12, and the long side 24 being chosen to maintain the tube in the rack and in a horizontal position during transportation. Further, while the rack is shown having several openings to hold several tubes at one time, it is contemplated that the rack can be used to hold and carry a single tube, jar, or petri dish such as for growing cultures and therefor would be fabricated with only a single opening.

What is claimed is:

1. A generally U-shaped rack for selectively supporting at least one elongated tube in alternately horizontally and vertically extending positions, without engaging the inserted end of the tube, said rack comprising:

a central support panel having first and second opposed edges and at least one tube-receiving opening therethrough, said central support panel functioning as a closed end to the U-Shaped structure of the rack a first end panel having a generally flat outer face for resting upon a supporting surface, said first end panel having first and second opposed edges, said first end panel being connected along the first of said first end panel opposed edges to said first edge of said central panel at an acute angle, a second end panel, shorter than said first end panel, and having first and second opposed edges, said second end panel being connected along said first of the second end panel opposed edges to said second edge of said central panel at an obtuse angle, said panels, which function as sides of the u-shaped structure of the rack, being constructed, arranged, proportioned and angled to one another so that, when the rack is supported upon said outer face of said first end panel, a tube having a cap on a first end and a closed second level supported by said central support panel extends generally horizontally, such that the tube first end is slightly elevated above said second end and when the rack is supported on both of said second opposed edges of said end side panels, a tube supported by said central support panel extends generally vertically.

2. The rack of claim 1 further including a handle connected to and extending outwardly from at least one of said panels, said handle oriented to support a tube mounted in the rack approximately in a horizontal manner when the rack is carried by the handle.

3. The rack of claim 2 wherein said handle extends from said central support panel at an angle of less than about 45° from the plane of the first end panel.

4. The rack of claim 2 wherein said handle is generally U-shaped having a central grasping portion and a pair of side connection portions extending therefrom, the side connecting portions being attached to said central support panel of the rack.

5. The rack of claim 1 wherein the second end panel is longer than the length of the portion of the tube that extends through and beyond the central panel.

6. The rack of claim 1 wherein said first and second end panels are generally parallel to one another.

7. The rack of claim 6 wherein said first end panel and said central panel are at an angle of less than about 60° to one another and said central panel and said second end panel are at an angle of more than about 120° to one another.

8. The rack of claim 1 wherein multiple elongated tubes are supported therein, each tube being supported in one of said openings, the tubes are tapered, and each tube has a flat side and a flat viewing panel aligned with the flat side, said opening including means that prevent the tubes seated in the openings from rotating and prevent the flat viewing panel of the tube from being positioned other than generally parallel to the plane of the first end panel.

9. The rack of claim 8 wherein the openings have a generally D-shape with the straight side of the D extending generally parallel to the plane of the first end panel.

10. The rack of claim 8 wherein said central support panel includes an extension about a portion of each said opening, each said extension extending outwardly from said central support panel in the same manner as said first end panel.

11. The rack of claim 10 wherein each of said extensions extends circumferentially around only a first portion of the associated opening, said first portion being closer to the first end panel than the remaining portion of the associated opening.

12. The rack of claim 11 wherein each of said extensions is a partial tubular section that extends circumferentially substantially beyond the center axis of the associated opening and is sufficiently resilient and flexible to facilitate the extension gripping and holding a tube when the tube is inserted into the associated opening.

13. The rack of claim 1 formed of a clear transparent material.

14. The rack of claim 1 formed of a polymeric material.

15. The rack of claim 14 wherein said material is an acrylic polymer.

16. The rack of claim 13 wherein said rack is in the form of a single molded piece.

17. The rack of claim 16 wherein the second end panel is a solid panel and said first end panel is generally U-shaped.

18. The rack of claim 3 wherein said first end panel and said central panel are at an angle of about 59° to one another and said central panel and said second end panel at an angle of about 121° to one another.

19. The rack of claim 18 wherein said openings are arranged in at least three rows with at least three openings in each row.

20. The rack of claim 5 wherein said openings support the tubes extending generally parallel to said first end panel.

21. The rack of claim 1 having a single opening for placement therein of a single container.

22. A rack for selectively supporting at least one elongated tube alternatively in a horizontally or vertically extending position without engaging the inserted end of the tube, said rack comprising:
a central support means having a pair of opposed edges and at least one tube-receiving opening therethrough,
a first end means having a generally flat outer face for resting upon a supporting surface, said first end means having a pair of opposed edges and being connected along one of its opposed edges to one of said opposed edges of said central means, said first end means extending generally transversely to said central support means,
a second end means having a pair of opposed edges and being connected along one of its opposed edges to the other of said opposed edges of said central means, said second end means extending generally transversely to said central support means,
a handle extending from the central support, the handle oriented at an angle to the central support
said handle and central and end means being constructed, arranged and proportional and so angled to one another that, when the rack is supported upon said outer face of said first end means, or carried by said handle, a tube having a cap on a first end and a closed second level supported in the tube-receiving opening in the central support means extends generally horizontally such that the tube first end is slightly elevated above said second end, and when the rack is supported on the free edges of the end means opposite the edges connected to the central means, a tube supported by the central support means extends generally vertically.

23. The rack of claim 22 for transporting at least one tube, said rack including a handle connected to and extending outwardly from at least one of said means.

24. The rack of claim 22 wherein said end means are both substantially longer than the length of the portion of the tube that extends through and beyond the central means.

25. The rack of claim 24 wherein said end means are generally parallel to one another.

26. The rack of claim 24 wherein said opening supports the tube extending generally parallel to said first end means.

27. The rack of claim 24 where said first end means is substantially longer than said second end means.

28. The rack of claim 24 wherein the rack has at least two tube-receiving openings, the rack supports at least two tubes, the tubes are tapered and each has a flat side and a flat viewing panel aligned with the flat side, said openings including means that prevent the tubes seated in the openings from rotating and that maintain the flat viewing panel of the tube generally parallel to the plane of the first end means.

29. The rack of claim 28 wherein an extension surrounds at least a portion of each of said openings, said extension extending generally parallel to the plane of the first end means.

30. The rack of claim 28 wherein each of said extensions extends circumferentially around only a portion of the associated opening, such portion of the opening being closest to the first end means.

31. The rack of claim 30 wherein each of said extensions is a partial elongated section that extends circumferentially substantially beyond the center axis of the associated opening and is sufficiently resilient and flexible to facilitate the extension gripping and holding the tube when the tube is inserted into the associated opening.

32. A generally U-shaped rack, in the form of a single molded piece of clear, transparent, acrylic polymer, for selectively supporting at least one elongated tube alternatively in a horizontally and a vertically extending position without engaging the inserted end of the tube, said rack comprising:

- a first end panel having a generally flat outer face for resting upon a supporting surface, said first end panel having first and second opposed edges;
- a central support panel having first and second opposed edges and being connected along the first of said opposed edges to said first edge of said first end panel at an angle of about 59°, said central support panel further including a set of D-shaped, tube-receiving openings therethrough, each opening configured with the straight side of the D extending generally parallel to said first opposed edge, to support, without permitting rotation, a tapered tube with a flat side and a flat viewing panel aligned with the flat side, said central support panel further including an extension about that portion of each said opening which is closer to said first end panel than the remainder of said opening, each said extension extending in a manner parallel to said first end panel,
- a second end panel, generally parallel to said first end panel and shorter than said first end panel but longer than the length of the portion of tube that extends through and beyond said central panel, having first and second opposed edges and being connected along the first of said second end panel opposed edges to said second edge of said central panel at an angle of about 121°,
- a generally U-shaped handle with a central grasping portion and a pair of side connection portions extending therefrom, said side connection portions being attached to said central support panel at an angle of less than about 45° from the plane of said first end panel,
- said panels and handle being constructed, arranged, proportioned and angled to one another such that, when said rack is supported upon said outer face of said first end panel, or the rack is held by the handle, a tube having a cap on a first end and a closed second level supported by said central support panel extends generally horizontally such that the tube first end is slightly elevated above said second end, and when said rack is supported on both of said second opposed edges of said side panels, a tube supported by said central support panel extends generally vertically.

* * * * *